United States Patent
Bou Chedid et al.

(10) Patent No.: US 9,512,061 B2
(45) Date of Patent: Dec. 6, 2016

(54) PROCESS FOR THE PREPARATION OF RACEMIC ALPHA-AMINO ACIDS

(71) Applicants: Roland Bou Chedid, Mannheim (DE); Alfred Oftring, Bad Duerkheim (DE); Wolfgang Staffel, Otterstadt (DE); Markus Christian Biel, Mannheim (DE); Johann-Peter Melder, Boehl-Iggelheim (DE); Christian Gruenanger, Mannheim (DE)

(72) Inventors: Roland Bou Chedid, Mannheim (DE); Alfred Oftring, Bad Duerkheim (DE); Wolfgang Staffel, Otterstadt (DE); Markus Christian Biel, Mannheim (DE); Johann-Peter Melder, Boehl-Iggelheim (DE); Christian Gruenanger, Mannheim (DE)

(73) Assignee: BASF SE, Ludwigshafen (DE)

( * ) Notice: Subject to any disclaimer, the term of this patent is extended or adjusted under 35 U.S.C. 154(b) by 473 days.

(21) Appl. No.: 13/720,027

(22) Filed: Dec. 19, 2012

(65) Prior Publication Data
US 2013/0158294 A1    Jun. 20, 2013

Related U.S. Application Data

(60) Provisional application No. 61/577,134, filed on Dec. 19, 2011.

(30) Foreign Application Priority Data

Jul. 9, 2012 (EP) .................................. 12175552

(51) Int. Cl.
C07C 227/08 (2006.01)
C07C 229/08 (2006.01)

(52) U.S. Cl.
CPC .................................. *C07C 227/08* (2013.01)

(58) Field of Classification Search
CPC .................................................. C07C 227/08
See application file for complete search history.

(56) References Cited

U.S. PATENT DOCUMENTS

| | | | |
|---|---|---|---|
| 4,350,826 A | 9/1982 | Edwards et al. | |
| 4,792,620 A * | 12/1988 | Paulik | B01J 31/0231 560/232 |
| 4,962,231 A | 10/1990 | Paul et al. | |
| 2004/0092725 A1 | 5/2004 | Hatakeda et al. | |
| 2004/0162434 A1 | 8/2004 | Hatakeda et al. | |
| 2012/0248370 A1 | 10/2012 | Oftring et al. | |
| 2012/0264973 A1 | 10/2012 | Baumann et al. | |
| 2012/0302783 A1 | 11/2012 | Baumann et al. | |

FOREIGN PATENT DOCUMENTS

| | | |
|---|---|---|
| CN | 102190591 | 9/2011 |
| EP | 0 295 550 A1 | 12/1988 |
| JP | 61-044850 | 3/1986 |
| JP | 6-329605 | 11/1994 |
| JP | 11049735 A * | 2/1999 |

OTHER PUBLICATIONS

International Search Report issued Apr. 2, 2013, in PCT/EP2012/075180.
European Search Report issued May 10, 2012, in European Patent Application No. 11194363.
Second Office Action issued Nov. 3, 2015, in Chinese patent application No. 201280062854.1 (English translation only).
Office Action issued Jun. 28, 2016, in Japanese patent application No. 2014-547849 (English translation only).

* cited by examiner

*Primary Examiner* — Paul A Zucker
(74) *Attorney, Agent, or Firm* — Oblon, McClelland, Maier & Neustadt, L.L.P.

(57) ABSTRACT

Process for the preparation of racemic α-amino acids or of glycine, wherein the corresponding α-hydroxycarboxylic acid, selected from hydroxyacetic acid, lactic acid, malic acid, α-hydroxyglutamic acid, isocitric acid, tartronic acid and tartaric acid, or at least one salt of the corresponding α-hydroxycarboxylic acid is reacted in the presence of at least one heterogeneous catalyst which comprises at least one transition metal, in the presence of hydrogen with at least one nitrogen compound (c), where the nitrogen compound (c) is selected from primary and secondary amines and ammonia.

19 Claims, No Drawings

PROCESS FOR THE PREPARATION OF RACEMIC ALPHA-AMINO ACIDS

The present invention relates to a process for the preparation of racemic α-amino acids or of glycine, wherein the corresponding α-hydroxycarboxylic acid, selected from hydroxyacetic acid, lactic acid, malic acid, α-hydroxyglutaric acid, isocitric acid, tartronic acid and tartaric acid, or at least one salt of the corresponding α-hydroxycarboxylic acid is reacted in the presence of at least one heterogeneous catalyst which comprises at least one transition metal, in the presence of hydrogen with at least one nitrogen compound (c), where nitrogen compound (c) is selected from primary and secondary amines and ammonia.

Furthermore, the present invention relates to mixtures of racemic α-amino acids and the corresponding α-hydroxycarboxylic acids.

Furthermore, the present invention relates to the use of mixtures according to the invention.

Amino acids have numerous fields of application. For example, L-amino acids are used for peptide synthesis and for protein synthesis. Though racemic amino acids are also valued intermediates.

The preparation of racemic amino acids by the Strecker synthesis is known per se. It is disadvantageous that with hydrocyanic acid and/or the corresponding cyanides, very toxic substances are required, which facilitate the need for special safety precautions.

US 2004/092725 discloses a process for synthesizing α-amino acids from corresponding α-hydroxycarboxylic acids by reaction with ammonia at high pressure and preferably at least 300° C. However, the yields are low. For example, the synthesis of glycine at 374° C. is disclosed with a yield of 4.3%, and the synthesis of α-alanine at 374° C. with a yield of 2.8%. However, yields of this type are unsatisfactory in industrial processes. Moreover, the products obtained are mostly dark in color and then require a complex purification process.

The object was thus to provide a process by means of which α-amino acids can be obtained in good yields. It was also the object to provide precursors for producing mixtures of detergents and cleaners including compositions for machine dishwashing which have a low or absolutely no developed tendency towards clumping.

Accordingly, the process defined at the start has been found, within the context of the present invention also called process according to the invention.

To carry out the process according to the invention, the starting material used is at least one α-hydroxycarboxylic acid, for example a mixture of two or three α-hydroxycarboxylic acids or one α-hydroxycarboxylic acid. α-Hydroxycarboxylic acid can be used in enantiomerically pure form or as a mixture of enantiomers, for example as racemate, meaning that different enantiomers of the α-hydroxycarboxylic acid in question exist.

α-Hydroxycarboxylic acid can be used as free acid or in partially or completely neutralized form. If the intention is to use α-hydroxycarboxylic acid in completely or partially neutralized form, then ammonium salts and alkali metal salts, such as, for example, potassium salts and in particular sodium salts, are preferred.

Examples of α-hydroxycarboxylic acids are hydroxyacetic acid, lactic acid, in particular L-lactic acid, malic acid, in particular L-malic acid, and α-hydroxyglutaric acid, also isocitric acid, tartronic acid and tartaric acid. Particularly preferred examples are racemic lactic acid, (−)-lactic acid and (+)-lactic acid.

In the case of the preparation of glycine, which is achiral, no racemate is obtained, but glycine.

In one embodiment of the present invention, the process according to the invention is carried out in an aqueous medium. This is to be understood as meaning that α-hydroxycarboxylic acid or its salt is suspended or dissolved in water or in a mixture that comprises to at least 75% by volume of water and can comprise in total up to 25% by volume of organic solvent, for example tetrahydrofuran or N,N-dimethylformamide, where % by volume is based on the total continuous phase. Alcohols are unsuitable as organic solvents. Preferably, no organic solvent, or only 0.1 to 5% by volume of organic solvent is used, based on the continuous phase.

In one embodiment of the present invention, the process according to the invention is carried out at a pH in the range from 4 to 14, preferably 6 to 14 and particularly preferably 8 to 13.5.

According to the invention, reaction is with at least one nitrogen compound (c), where the nitrogen compound (c) is selected from primary amines, preferably secondary amines and even more preferably ammonia. Examples of primary amines are in particular $C_1$-$C_{10}$-alkylamines, for example methylamine, ethylamine, isopropylamine, tert-butylamine, n-decylamine, also aromatic amines such as aniline, $C_3$-$C_7$-cycloalkylamines such as, for example, cyclohexylamine and monoethanolamine. Examples of secondary amines are di-$C_1$-$C_{10}$-alkylamines, in particular dimethylamine, diethylamine and diisopropylamine, also di-$C_2$-$C_4$-hydroxyalkyleneamines, in particular diethanolamine, also mono-$C_1$-$C_{10}$-alkylmono-$C_2$-$C_4$-hydroxyalkyleneamines, for example N-methyl-N-ethanolamine, also cyclic secondary amines such as piperidine and morpholine. Further suitable nitrogen compounds (c) are iminodicarboxylic acids, in particular iminodiacetic acid.

In a preferred embodiment of the present invention, the nitrogen compound (c) selected is ammonia, i.e. reaction is with ammonia. Ammonia can be added to the reaction mixture in the form of liquid ammonia, gaseous ammonia or ammoniacal water ("$NH_4OH$"). If it is desired to add ammonia in the form of an ammonium salt, then it is preferred to add ammonia in combination with at least one strong base, for example in combination with NaOH or KOH. It is preferred to add ammonia in the form of liquid ammonia or ammoniacal water.

In one embodiment, α-hydroxycarboxylic acid and nitrogen compound (c) are used in a molar ratio in the range from 1:1 to 1:100, preferably in the range from 1:2 to 1:50, particularly preferably in the range from 1:3 to 1:30. Here, the fraction of nitrogen compound (c) refers to the sum of all nitrogen compounds (c).

In one embodiment, α-hydroxycarboxylic acid and ammonia are used in a molar ratio in the range from 1:1 to 1:100, preferably in the range from 1:2 to 1:50, particularly preferably in the range from 1:3 to 1:30.

The process according to the invention is carried out in the presence of hydrogen, i.e. $H_2$. In one embodiment of the present invention, the process according to the invention is carried out such that in total a molar ratio of α-hydroxycarboxylic acid to hydrogen in the range from 1:1 to 1:90, preferably 1:2 to 1:30, is established. In another embodiment, a molar ratio of α-hydroxycarboxylic acid to hydrogen in the range from 2:1 to 1.01:1 is established.

In one embodiment of the present invention, hydrogen can be diluted by means of a gas that is inert under the reaction conditions of the process according to the invention, for example with nitrogen or with at least one noble gas, for example with argon.

The process according to the invention is carried out in the presence of at least one heterogeneous catalyst which comprises at least one transition metal. The heterogeneous catalysts here may be:
(i) metal-containing catalysts supported on a solid support which is present in particulate form,
(ii) metal-containing catalysts supported on a solid support which is in nonparticulate form,
(iii) support-free catalytically active particles.

Within the context of the present invention, the term catalyst here comprises transition metal, which serves as catalytically active species ("main metal"), or optionally a precursor thereof, also optionally present support and optionally present doping.

"Solid support" is to be understood here as meaning those materials which are solid under the reaction conditions of the process according to the invention and which are appropriate for the shaping of the heterogeneous catalyst.

"Present in particulate form" is to be understood as meaning that the support in question is present in the form of particles, the average diameter of which is in the range from 0.1 μm to 2 mm, preferably 0.001 to 1 mm, preferably in the range from 0.005 to 0.5 mm, in particular 0.01 to 0.25 mm.

"Present in nonparticulate form" is to be understood as meaning that the support has, in at least one dimension (width, height, depth), more than 2 mm, preferably at least 5 mm, where at least one further dimension, for example one or both further dimensions, can be less than 2 mm in size, for example in the range from 0.1 μm to 2 mm. In another variant, support present in nonparticulate form has three dimensions which have a dimension of more than 2 mm, preferably at least 5 mm. A suitable upper limit is, for example, 10 m, preferably 10 cm.

Examples of supports which are present in nonparticulate form are metal meshes, for example steel meshes or nickel meshes, also wires such as steel wires or nickel wires, also moldings, for example beads, Raschig rings, strands and tablets.

In one embodiment of the present invention, catalyst is used in the form of moldings, for example in the form of tablets or strands.

Examples of particularly suitable dimensions of moldings are tablets with dimensions 6.3 mm, 3.3 mm, 2.2 mm, and strands with a diameter in the range from 1.5 to 3 mm.

Examples of supports which are present in particulate form are powders, which may be free-flowing or suspended.

Examples of materials from which supports which are present in particulate form may be made are $Al_2O_3$, $SiO_2$, aluminosilicates, hydrotalcite, $TiO_2$, $ZrO_2$, activated carbon, in particular $Al_2O_3$, $ZrO_2$ and $TiO_2$.

Examples of support-free catalytically active particles (iii) are Raney metals, for example Raney-copper, Raney-nickel and Raney-cobalt. Support-free catalytically active particles can be present for example as sponge or skeletal catalysts.

Besides support and transition metal, the catalyst can comprise one or more molding agents, for example graphite or stearic acid.

Examples of transition metals which are suitable as catalytically active species ("main metal") in metal-containing catalyst for the process according to the invention are transition metals of groups 4 to 12 of the Periodic Table of the Elements, and specifically preferably transition metals of the first periods of groups 4 to 12 of the Periodic Table of the Elements, i.e. from Ti to Zn, and also transition metals of groups 8 to 11 in all periods of the Periodic Table of the Elements. Particularly preferred transition metals are Co, Ni and Cu.

Transition metal in catalyst which is used for the process according to the invention can be doped, for example with one or more other transition metals such as Zr or Ti, or with Ca, with Sn, with Al or with Na. Doping is to be understood here as meaning amounts of doped transition metal or Na, Al or Ca which are incorporated in the range from 0.1 to 2 mol % of transition metal or Na, Sn, Al or Ca, based on main metal. Within the context of the present invention, however, customary accompanying trace elements originating from the production of main metal are deemed as being excluded from a doping.

In one embodiment of the present invention, heterogeneous catalysts are selected from Raney metals and transition metal applied to a solid support. A preferred transition metal (main metal) is selected from Ni, Cu and Co.

To produce a catalyst that is suitable for the process according to the invention, and to store it, a transition metal is generally used as precursor, namely as compound, for example as oxide, hydroxide or oxidehydroxide, or as alloy, and the catalyst is activated before carrying out the process according to the invention or in situ, preferably by means of reduction or by removing at least one component of the alloy in question. Preferably, the transition metal in the heterogeneous catalyst is present while the process according to the invention is carried out proportionately at least for part of the time in oxidation state zero.

In one embodiment of the present invention, catalysts are selected from those materials in particulate form whose mass—in each case determined prior to activation with hydrogen—comprises:
in total in the range from 15 to 80% by weight of oxygen-containing compound(s) of aluminum, calculated as $Al_2O_3$, preferably 30 to 70% by weight, particularly preferably 35 to 65% by weight,
in total in the range from 5 to 35% by weight of oxygen-containing compound(s) of nickel, calculated as NiO, preferably in the range from 10 to 30% by weight, particularly preferably in the range from 12 to 28% by weight, very particularly preferably 15 to 25% by weight,
in total in the range from 5 to 35% by weight of oxygen-containing compound(s) of cobalt, calculated as CoO, preferably in the range from 10 to 30% by weight, particularly preferably in the range from 12 to 28% by weight, very particularly preferably 15 to 25% by weight,
in total in the range from 1 to 20% by weight of oxygen-containing compound(s) of copper, calculated as CuO, preferably 2 to 18% by weight, particularly preferably 5 to 15% by weight,
in total in the range from 0.2 to 5% by weight of oxygen-containing compound(s) of tin, calculated as SnO, preferably in the range from 0.4 to 4.0% by weight, particularly preferably in the range from 0.6 to 3.0% by weight, very particularly preferably in the range from 0.7 to 2.5% by weight.

In one embodiment of the present invention, catalysts are selected from those materials in particulate form whose mass—in each case determined prior to activation with hydrogen—comprises:
22 to 45% by weight, preferably 25 to 40% by weight, of oxygen-containing compounds of zirconium, calculated as $ZrO_2$, 1 to 30% by weight, preferably 2 to 25% by weight, particularly preferably 5 to 15% by weight, of oxygen-containing compounds of copper, calculated as CuO, 5 to 50% by weight, preferably 15 to 45% by weight, particularly preferably 25 to 40% by weight, of oxygen-containing compounds of nickel, calculated as NiO, 5 to 50% by weight of oxygen-containing compounds of cobalt, calculated as CoO, 0 to 10% by weight of oxygen-containing compounds of aluminum and/or manganese, where the weight ratio of zirconium, calculated as $ZrO_2$, to aluminum and/or manganese, calculated as $Al_2O_3$ and/or $MnO_2$, is preferably at least 2.5, very particularly preferably 0% by weight of oxygen-containing compounds of aluminum and/or manganese, 0 to 5% by weight, preferably 0% by weight, of oxygen-containing compounds of molybdenum, calculated as $MoO_3$.

In one embodiment of the present invention, catalysts are selected from those materials in particulate form whose mass—in each case determined prior to activation with hydrogen—comprises:

50 to 95% by weight, preferably 55 to 85% by weight, particularly preferably 60 to 80% by weight, of oxygen-containing compounds of zirconium, calculated as $ZrO_2$, 5 to 50% by weight, preferably 15 to 45% by weight, particularly preferably 20 to 40% by weight, of oxygen-containing compounds of nickel, calculated as NiO.

In one embodiment of the present invention, the molar ratio of nickel to copper is greater than 1, particularly preferably greater than 1.2, very particularly preferably in the range from 1.8 to 8.5.

Preferably, the catalytically active mass of catalyst used in the process according to the invention comprises no rhenium, no ruthenium, no iron and/or no zinc, in each case neither in metallic (oxidation state=0) nor in ionic (oxidation state≠0).

In one embodiment of the present invention, catalyst suitable for the process according to the invention has a BET surface area in the range from 1 to 1000 m²/g, preferably from 10 to 500 m²/g, measured by $N_2$ adsorption in accordance with DIN 66131.

Different processes are possible for producing preferred catalysts of variant (i) and (ii) used in the process according to the invention. Suitable catalysts of variant (i) and (ii) are obtainable, for example, by kneading pulverulent mixtures of the hydroxides, carbonates, oxides and/or other salts of the components with water and subsequent extrusion and tempering (heat treatment) of the resulting mass.

Preferably, precipitation methods are used for producing the catalysts of variant (i) and (ii) used in the process according to the invention. Thus, preferred catalysts can be obtained for example by means of a joint precipitation of nickel, cobalt, copper and tin components from an aqueous salt solution comprising these elements by means of bases in the presence of a slurry of a sparingly soluble, oxygen-containing aluminum, titanium, silicon and/or zirconium compound (precipitate) and subsequent washing, drying and calcination of the resulting precipitate. Sparingly soluble, oxygen-containing aluminum, titanium, silicon and/or zirconium compounds which can be used are, for example, the oxides, oxide hydrates, phosphates, borates and silicates thereof. Slurries of the sparingly soluble oxygen-containing aluminum, titanium, silicon and/or zirconium compounds can be prepared by suspending finely particulate powders of compounds of this kind in water with vigorous stirring. Slurries of sparingly soluble oxygen-containing aluminum, titanium, silicon and/or zirconium compounds are preferably prepared by precipitating the corresponding sparingly soluble oxygen-containing aluminum, titanium, silicon and zirconium compounds from aqueous solutions of aluminum, titanium, silicon and/or zirconium compounds by means of base.

Preferably, catalysts of variant (i) and (ii) used in the process according to the invention are prepared via a joint precipitation (mixed precipitation) of all of their components. For this purpose, an aqueous salt solution comprising the catalyst components is expediently admixed, at elevated temperature and with stirring, with an aqueous base—for example sodium carbonate, sodium hydroxide, potassium carbonate or potassium hydroxide—until the precipitation is complete. It is also possible to work with alkali metal-free bases such as ammonia, ammonium carbonate, ammonium hydrogencarbonate, ammonium carbamate, ammonium oxalate, ammonium malonate, urotropin, urea, etc. The type of salts used is generally not critical: since in this procedure what matters is primarily the solubility in water of the salts, one criterion is their good solubility in water required for producing the relatively highly concentrated salt solutions. It is considered to be self explanatory that when selecting the salts of the individual components, naturally only salts are selected with those anions which do not lead to disturbances, whether by causing undesired precipitations or by hindering or preventing precipitation as a result of complexation.

The precipitates obtained during these precipitation reactions are generally chemically nonuniform and consist inter alia of mixtures of the oxides, oxide hydrates, hydroxides, carbonates, and insoluble and basic salts of the metals used. For the filterability of the precipitates, it may prove favorable if they are aged, i.e. if they are left to themselves for some time after the precipitation, optionally at elevated temperature and while passing air through.

The precipitates obtained after precipitation processes can be further processed to give catalysts of variant (i) and (ii) used in the process according to the invention by methods known per se. Initially, the precipitates are washed. The content of alkali metal which has been introduced by the (mineral) base possibly used as precipitating agent can be influenced via the duration of the washing and via the temperature and amount of the wash water. In general, the content of alkali metal will decrease by extending the washing or by increasing the temperature of the wash water. After the washing, the precipitates can be dried, generally at 80 to 200° C., preferably at 100 to 150° C., and then calcined. The calcination can be carried out at temperatures between 300 and 800° C., preferably at 400 to 600° C., in particular at 420 to 550° C.

In another embodiment, catalysts of variant (i) and (ii) used in the process according to the invention can be produced by impregnating aluminum oxide ($Al_2O_3$), titanium dioxide ($TiO_2$), silicon dioxide ($SiO_2$), zirconium dioxide ($ZrO_2$), which is present, for example, in the form of powders or moldings, such as strands, tablets, beads or rings or mixtures of at least two of the aforementioned oxides with transition metal salt solution.

Aluminum oxide is used, for example, in the amorphous, gamma, theta and/or delta form, as aluminum oxohydroxide (boehmite), preferably in the gamma form.

Zirconium dioxide can be used, for example, in an amorphous, monoclinic, tetragonal or cubic modification, preference being given to the monoclinic, the tetragonal and the cubic modification. Particular preference is given to the monoclinic modification.

Moldings can be produced by methods known per se.

In one embodiment of the present invention, 0.1 to 120% by weight of catalyst is used, based on α-hydroxycarboxylic acid.

In one embodiment of the process according to the invention, it is carried out at a temperature in the range from 150 to 280° C., preferably 170 to 250° C.

In one embodiment of the process according to the invention, it is carried out at a pressure in the range from 10 to 300 bar, preferably 100 to 250 bar, particularly preferably from 150 to 200 bar.

The process according to the invention can be carried out batchwise, continuously or semi-continuously.

In one embodiment of the present invention, the entire reaction mixture or certain components of the reaction mixture can be circulated, for example nitrogen-containing compound (c), in particular ammonia, or solution of α-hydroxycarboxylic acid.

In one embodiment of the present invention, the process according to the invention can be carried out batchwise at an essentially constant temperature, for example at a temperature which fluctuates by 10° C. or less during the process according to the invention, preferably by 5° C. or less.

In one embodiment of the present invention, the process according to the invention is carried out over a duration in the range from 1 minute to 48 hours. If the desire is to carry out the process according to the invention continuously, then duration is to be understood as meaning the average residence time.

In one embodiment of the present invention, the process according to the invention is carried out as suspension of at least one catalyst according to variant (i) or (iii), and specifically with a reaction time in the range from 1 to 48 hours, preferably 2 to 24 hours.

In another embodiment of the present invention, the process according to the invention is carried out with a catalyst according to variant (ii), and specifically with a reaction time in the range from 1 minute to 10 hours, preferably 30 minutes to 5 hours.

When calculating the time, periods of time which are used for activities such as heating, cooling, working up the reaction mixture, isolating racemic α-amino acid, decompressing or activating the catalyst, should not be taken into consideration.

In one embodiment of the present invention, mixing can be used to carry out the process according to the invention, for example by means of stirring, shaking, rolling, circulating, pumping via static mixers or pneumatic mixers.

Without any intention of giving preference to a specific theory, it is assumed that in the course of the process according to the invention α-hydroxycarboxylic acid is firstly oxidized, i.e. dehydrogenated, to the α-ketocarboxylic acid, which is then converted to the corresponding α-iminocarboxylic acid and is then reduced to racemic α-aminocarboxylic acid.

This gives a reaction mixture which comprises water and racemic α-amino acid or salt of racemic α-amino acid and can have further constituents, for example catalyst (residues), starting material such as α-hydroxycarboxylic acid or nitrogen compound (c), in particular ammonia, or furthermore decomposition products of α-hydroxycarboxylic acid, for example propionic acid, acetic acid or formic acid.

In one embodiment of the present invention, the resulting reaction mixture is worked up. In a specific embodiment of the present invention, racemic α-amino acid or a salt of racemic α-amino acid is isolated.

For the work-up, one or more of the following activities, for example, can be carried out:

(i) deactivate catalyst,
(ii) separate off catalyst, which may be active or deactivated, for example by filtration, for example cake filtration or cross flow filtration, or by sedimentation or centrifugation,
(iii) completely or partially remove water and nitrogen compound (c), in particular ammonia, for example by evaporation, distillation or spray-drying,
(iv) neutralize nitrogen compound (c) or in particular ammonia with acid, in particular with Brönsted acid, for example with sulfuric acid or hydrochloric acid,
(v) separate off by-product which can be formed for example as a result of reduction of α-hydroxycarboxylic acid used,
(vi) adjust pH, for example with Brönsted acid or Brönsted base,
(vii) separate off α-amino acid from unreacted α-hydroxycarboxylic acid by means of ion exchanger.

In one embodiment of the present invention, racemic α-amino acid or salt of racemic α-amino acid that is produced is recrystallized for the purposes of purification. Various solvents can be used for the recrystallization. Of suitability are, for example, water and water-containing mixtures, for example mixtures of water with ethanol. Preferably, recrystallization is from water or aqueous bases which have a pH in the range from 7.1 to 14, preferably 9 to 12. Suitable aqueous bases are dilute potassium hydroxide solution and in particular dilute sodium hydroxide solution.

Recrystallization can be carried out one or more times. Crystallized racemic α-amino acid or crystallized salt of racemic α-amino acid can be separated off from the mother liquor, for example by decantation or filtration or a combination of filtration and decantation.

In one embodiment, pure racemic α-amino acid or pure salt of racemic α-amino acid, for example pure sodium salt or pure potassium salt, or partially neutralized pure racemic α-amino acid is obtained.

Another embodiment of the present invention gives mixtures comprising
(a) in the range from 91 to 99.9% by weight of a racemic α-amino acid, preferably 95 to 99.9% by weight,
(b) in the range from 0.1 to 9% by weight of the corresponding α-hydroxycarboxylic acid, selected from hydroxyacetic acid, lactic acid, malic acid, 2-hydroxyglutaric acid, isocitric acid, tartronic acid and tartaric acid, preferably 0.5 to 5% by weight, in in each case pure form or partially or completely neutralized, preferably with potassium or ammonium or in particular with sodium,
where data in % by weight are in each case based on the total mixture,
and which are likewise provided by the present invention.

Racemic α-amino acid is selected from glycine and in each case the racemate of alanine, aspartic acid, glutamic acid, -aminopropane-1,2,3-tricarboxylic acid, 2-aminomalonic acid, 2-amino-3-hydroxysuccinic acid and 2,3-diaminosuccinic acid.

Corresponding α-hydroxycarboxylic acid (b) can be enantiomer-enriched or preferably racemic.

The proof that racemic α-amino acid (a) is the racemate is provided, for example, by polarimetry.

In a preferred embodiment of the present invention, in mixtures according to the invention,
racemic α-amino acid (a) is selected from racemic α-alanine and
α-hydroxycarboxylic acid (b) is selected from preferably racemic lactic acid in in each case pure form or partially or completely neutralized, preferably with potassium or ammonium or in particular sodium.

Mixtures according to the invention can be prepared, for example, by the process according to the invention.

The present invention further provides the use of mixtures according to the invention for producing complexing agents. The present invention further provides a process for producing complexing agents using at least one mixture according to the invention.

Mixtures according to the invention can be used, for example, for producing complexing agents. For example, mixtures of racemic α-alanine and racemic lactic acid can be used in order to produce racemic methylglycinediacetic acid (MGDA), for example by ethoxylation and subsequent oxidation of the alcoholic $CH_2$—OH groups, or by Strecker synthesis using HCN/HCHO. The fraction of lactic acid, in particular of racemic lactic acid, is not troublesome in such a case during the production of MGDA. A mixture of lactic acid and racemic MGDA, as pure acid or completely or partially neutralized, for example with sodium or potassium, is obtained.

The present invention further provides formulations comprising at least one mixture according to the invention.

The present invention specifically provides a mixture comprising
(a) in the range from 0.1 to 5% by weight of lactic acid, preferably as racemate,
(b) in the range from racemic 95 to 99.9% by weight of N,N-methylglycinediacetic acid, in each case pure form or partially or completely neutralized, preferably with potassium or ammonium or in particular sodium.

The invention is illustrated by working examples.

Unless expressly stated otherwise, data in % are percent by weight.

In the context of the description, the term "catalyst" also refers to inactivated catalysts.

I. Preparation of Catalysts

I.1 Preparation of catalyst I.1

The following were introduced simultaneously, with stirring, into a stirred vessel heated to 65° C.:
an aqueous solution of nickel nitrate, cobalt nitrate, copper nitrate, aluminum nitrate and tin(II) chloride, which comprised converted 3.9% Ni, 3.9% Co, 1.9% Cu, 5.5% $Al_2O_3$ and 0.5% Sn ("transition metal salt solution"), and
a 20% strength by weight aqueous sodium carbonate solution.

To this was fed the transition metal salt solution in a constant stream. The metering of the 20% strength by weight aqueous sodium carbonate solution was regulated such that the pH of 5.7, measured using a glass electrode, was kept constant. By precipitating nickel, cobalt, aluminum, copper and tin compounds, a suspension was formed. The temperature of the suspension was 65° C. When the precipitation was complete, air was blown in for one hour, then the pH of the suspension was adjusted to a value of 7.4 using sodium carbonate solution. The suspension obtained in this way was filtered and the filter cake was washed with demineralized water until the electrical conductivity of the filtrate was ca. 20 mS. The filter cake was then dried in a drying cabinet at a temperature of 150° C. The hydroxide carbonate mixture obtained in this way was then calcined at a temperature of 500° C. over 4 hours. The catalyst mass was then mixed with 3% by weight of graphite and shaped to give 3.3 mm tablets. The tablets obtained in this way were reduced in hydrogen at a temperature of 280 to 300° C. over at least 12 hours. The passivation of the reduced catalyst was carried out at room temperature in "dilute" air ($O_2$ content of at most 5% by volume, air in $N_2$). The composition of the catalyst I.1 obtained in this way is shown in Table I.

I.2 Preparation of Catalyst I.2

The following were introduced simultaneously, with stirring, into a stirred vessel heated to 65° C.:
an aqueous solution of nickel nitrate, cobalt nitrate, copper nitrate and zirconium acetate, which comprised converted 7% by weight of NiO, 7% by weight of CoO, 3.25% by weight of CuO and 7.75% by weight of $ZrO_2$ ("transition metal salt solution"), and
a 20% strength by weight aqueous sodium carbonate solution.

To this was fed the transition metal salt solution in a constant stream. The metering of the 20% strength by weight aqueous sodium carbonate solution was regulated such that the pH of 7.5, measured using a glass electrode, was kept constant. By precipitating nickel, cobalt, copper and zirconium compounds, a suspension was formed. The temperature of the suspension was 65° C. When the precipitation was complete, the suspension obtained in this way was filtered and the filter cake was washed with demineralized water until the electrical conductivity of the filtrate was ca. 20 mS. The filter cake was then dried in a drying cabinet at a temperature of 120° C. The hydroxide carbonate mixture obtained in this way was then calcined at a temperature of 400° C. over 2 hours. The catalyst mass was then shaped to give 3·3 mm tablets. The tablets obtained in this way were reduced in hydrogen at a temperature of 280 to 300° C. over at least 12 hours. The passivation of the reduced catalyst was carried out at room temperature in "dilute" air ($O_2$ content of at most 5% by volume, air in $N_2$). The composition of the catalyst I.2 obtained in this way is shown in Table I.

TABLE I

Composition of catalysts I.1 and I.2

| Catalyst *) | Ni % | Co % | Cu % | Sn % | BET $m^2/g$ | Support |
|---|---|---|---|---|---|---|
| I.1 | 18.6 | 17.3 | 10.6 | 1.1 | 187 | $Al_2O_3$ |
| I.2 | 28 | 28 | 13 | — | 75 | $ZrO_2$ |

*): catalyst composition in % by weight; remainder to 100% by weight is the support.

II. Preperation of α-Alanine (Racemic)

II.1 Preparation of α-Alanine with a Raney Nickel Catalyst 10 g of Raney nickel as catalyst, 74 g of a 36% by weight aqueous solution of sodium salt of L-lactic acid and 45 g of liquid ammonia were introduced as initial charge in a 300 ml autoclave. 20 bar of hydrogen were injected and the mixture was heated to 200° C. The pressure was then raised to 200 bar by injecting further hydrogen. The mixture was then stirred for 24 hours at 200 bar hydrogen and 200° C. After 16 hours, an aliquot was taken and the conversion was determined at 64%, based on lactic acid, and determined by $^1$H NMR spectroscopy. After a total of 24 hours, the mixture was cooled to room temperature and decompressed, and the catalyst was filtered off and 45 g of water and unreacted ammonia were distilled off.

This gave a mixture comprising 79 mol % of racemic α-alanine and 21 mol % of racemic lactic acid, in each case as sodium salt. The residual moisture was 20% by weight, based on the sum of racemic α-alanine and racemic lactic acid, in each case as sodium salt.

II.2 Preparation of α-Alanine with a Raney Nickel Catalyst 10 g of Raney nickel as catalyst, 74 g of a 36% strength by weight aqueous solution of sodium salt of L-lactic acid and 45 g of liquid ammonia were introduced as initial charge in a 300 ml autoclave. 20 bar of hydrogen were injected in and the mixture was heated to 210° C. The pressure was then increased to 200 bar by injecting further hydrogen. The mixture was then stirred for 24 hours at 200 bar hydrogen and 210° C. After 16 hours, an aliquot was taken and the conversion was determined at 89%, based on lactic acid, and determined by $^1$H NMR spectroscopy. After a total of 24 hours, the mixture was cooled to room temperature and decompressed, and the catalyst was filtered off, and 45 g of water and unreacted ammonia were distilled off.

This gave a mixture according to the invention GM-AM.1, comprising 92 mol % of racemic α-alanine and 8 mol % of racemic lactic acid, in each case as sodium salt. That corresponds to a weight ratio of 91.9% by weight of racemic α-alanine to 8.1% by weight of racemic lactic acid, based in each case on the free acid.

GM-AM.1 could be processed very readily to produce mixtures of (±)-MGDA and racemic lactic acid.

II.3 Preparation of α-Alanine with the Help of an Ni—Co—Cu—Sn Catalyst 10 g of catalyst I.1 were charged to a catalyst basket made of stainless steel. The catalyst basket filled in this way was placed into a 300 ml autoclave and treated with hydrogen at 250° C. over a period of 24 hours. The catalyst was thereby activated. The system was decompressed and cooled to room temperature and 74 g of a 36% strength by weight aqueous solution of sodium salt of L-lactic acid and 45 g of liquid ammonia were added. 20 bar of hydrogen was injected and the mixture was heated to 200° C. The pressure was then raised to 200 bar by injecting further hydrogen. The mixture was then stirred for 24 hours at 200 bar hydrogen and 200° C. After 16 hours, an aliquot was removed and the conversion was determined at 64%, based on lactic acid, and determined by $^1$H NMR spectroscopy. After a total of 24 hours, the system was cooled to room temperature and decompressed, and the catalyst basket was removed together with catalyst, and 45 g of water and unreacted ammonia were distilled off.

This gave a mixture comprising 79 mol % of racemic α-alanine and 21 mol % of racemic lactic acid, in each case as sodium salt. The residual moisture was 15% by weight, based on the sum of racemic α-alanine and racemic lactic acid, in each case as sodium salt.

An analysis of the gas space above the reaction mixture revealed a fraction of 0.15% by volume of methane.

II.4 Preparation of α-Alanine with the Help of an Ni—Co—Cu—Sn Catalyst 10 g of catalyst I.1 were charged to a catalyst basket made of stainless steel. The catalyst basket filled in this way was placed into a 300 ml autoclave and treated with hydrogen at 250° C. over a period of 24 hours. The catalyst was thereby activated. The system was decompressed and cooled to room temperature, and 74 g of a 36% strength by weight aqueous solution of sodium salt of L-lactic acid and 45 g of liquid ammonia were added. 20 bar of hydrogen was injected and the mixture was heated to 210° C. The pressure was then raised to 200 bar by injecting further hydrogen. The mixture was stirred for 24 hours at 200 bar hydrogen and 210° C. After 16 hours, an aliquot was taken and the conversion was determined at 85%, based on lactic acid, and determined by $^1$H NMR spectroscopy. After a total of 24 hours, the mixture was cooled to room temperature and decompressed, the catalyst basket was removed together with catalyst, and 45 g of water and unreacted ammonia were distilled off.

This gave a mixture according to the invention comprising 92 mol % of racemic α-alanine and 8 mol % of racemic lactic acid, in each case as sodium salt. It corresponded in its composition to mixture according to the invention GM-AM.1 from example 2.

II.5 Continuous Preparation of α-Alanine with the Help of an Ni—Co—Cu Catalyst 500 ml of catalyst I.2 were charged to a fixed-bed reactor, dimensions: length 2 m, circular diameter: 3 cm, with return pump. The catalyst was treated with hydrogen at 280° C. without pressure over a period of 24 hours. The catalyst was thereby activated. The fixed-bed reactor was then operated such that the fixed bed was operated continuously from bottom to top with 91 g/h of a 55% by weight aqueous solution of sodium salt of L-lactic acid, 227 g/h of gaseous ammonia and 100 l/h (stp) of hydrogen. The return pump required 502 g/h of the reaction mixture. A temperature of 210° C. and a pressure of 200 bar were established. After decompression, an aqueous solution was obtained comprising the sodium salts of racemic α-alanine and racemic lactic acid in the molar ratio 83:17.

II.6 Continuous Preparation of α-Alanine with the Help of an Ni—Co—Cu Catalyst 500 ml of catalyst I.2 were charged to a fixed-bed reactor, dimensions: length 2 m, circular diameter: 3 cm. The catalyst was treated with hydrogen at 280° C. without pressure over a period of 24 hours. The catalyst was thereby activated. The fixed-bed reactor was then operated such that the fixed bed was operated continuously from bottom to top with 69 g/h of a 60% by weight aqueous solution of sodium salt of L-lactic acid, 77 g/h of gaseous ammonia and 50 l/h (stp) of hydrogen. A temperature of 200° C. and a pressure of 50 bar were established. The system was decompressed via a control valve, giving a mixture according to the invention GM-AM.6, comprising racemic α-alanine and racemic lactic acid, in each case as sodium salt, in the molar ratio 92:8.

GM-AM.6 could be processed very readily to produce mixtures of (±)-MGDA and racemic lactic acid.

The invention claimed is:

1. A process for producing a mixture comprising:
    (a) from 91 to 99.9% by weight of a racemic α-amino acid, and
    (b) from 0.1 to 9% by weight of the corresponding racemic α-hydroxycarboxylic acid,
    wherein said racemic α-amino acid (a) and said racemic α-hydroxycarboxylic acid (b) are completely neutralized, wherein the racemic α-amino acid is at least one selected from the group consisting of alanine, aspartic acid, glutamic acid, 2-aminopropane-1,2,3-tricarboxylic acid, 2-aminomalonic acid, 2-amino-3-hydroxy-succinic acid, and 2,3-diaminosuccinic acid, and wherein % by weight of each (a) and (b) are based in each case on the total weight of the mixture,
    the process comprising:
    reacting the corresponding racemic α-hydroxycarboxylic acid or at least one salt of the corresponding racemic α-hydroxycarboxylic acid in the presence of at least one heterogeneous catalyst which comprises a transition metal, and in the presence of hydrogen with at least one nitrogen compound (c),
    wherein the at least one nitrogen compound (c) is selected from the group consisting of a primary and secondary amine and ammonia.

2. The process according to claim 1, wherein the at least one heterogeneous catalyst is selected from the group consisting of a Raney metal and a transition metal applied to a solid support.

3. The process according to claim 2, wherein the transition metal is selected from the group consisting of Ni, Cu and Co.

4. The process according to claim 2, wherein the transition metal is present during the process at least for part of the time in oxidation state zero.

5. The process according to claim 1, wherein the nitrogen compound (c) is ammonia.

6. The process according to claim 1, wherein the process is carried out at a temperature in the range from 150 to 280° C.

7. The process according to claim 1, wherein the corresponding racemic α-hydroxycarboxylic acid is selected from the group consisting of racemic lactic acid, (−)-lactic acid and (+)-lactic acid.

8. The process according to claim 1, wherein the salts of the corresponding racemic α-hydroxycarboxylic acid is selected from an alkali metal salt and an ammonium salt of the corresponding racemic α-hydroxycarboxylic acid.

9. The process according to claim 1, wherein the process is carried out at a pressure in the range from 10 to 300 bar.

10. The process according to claim 1, wherein the process is carried out in an aqueous medium.

11. The process according to claim 1, further comprising: purifying produced racemic α-amino acid by recrystallization.

12. A mixture, comprising:
(a) from 91 to 99.9% by weight of a racemic α-amino acid, and
(b) from 0.1 to 9% by weight of the corresponding racemic α-hydroxycarboxylic acid,
wherein said racemic α-amino acid (a) and said racemic α-hydroxycarboxylic acid (b) are completely neutralized,
wherein the racemic α-amino acid is at least one selected from the group consisting of alanine, aspartic acid, glutamic acid, 2-aminopropane-1,2,3-tricarboxylic acid, 2-aminomalonic acid, 2-amino-3-hydroxysuccinic acid, and 2,3-diaminosuccinic acid, and
wherein % by weight of each (a) and (b) are based in each case on the total weight of the mixture.

13. The mixture according to claim 12, wherein the racemic α-amino acid (a) is racemic α-alanine and
the corresponding racemic α-hydroxycarboxylic acid (b) is racemic lactic acid.

14. A formulation, comprising the mixture according to claim 12.

15. A mixture, comprising:
(a) from 95 to 99.9% by weight of a racemic α-amino acid, and
(b) from 0.1 to 5% by weight of the corresponding racemic α-hydroxycarboxylic acid,
wherein said racemic α-amino acid (a) and said racemic α-hydroxycarboxylic acid (b) are partially or completely neutralized,
wherein the racemic α-amino acid is at least one selected from the group consisting of alanine, aspartic acid, glutamic acid, 2-aminopropane-1,2,3-tricarboxylic acid, 2-aminomalonic acid, 2-amino-3-hydroxysuccinic acid, and 2,3-diaminosuccinic acid, and
wherein % by weight of each (a) and (b) are based in each case on the total weight of the mixture.

16. The mixture according to claim 12, wherein the amount of the corresponding racemic α-hydroxycarboxylic acid (b) is from 0.5 to 5 weight %.

17. The mixture according to claim 12, wherein the amount of the racemic α-amino acid (a) is from 95 to 99.9%.

18. The mixture according to claim 12, wherein the corresponding α-hydroxycarboxylic acid is selected from the group consisting of hydroxyacetic acid, lactic acid, malic acid, α-hydroxyglutaric acid, isocitric acid, tartronic acid, and tartaric acid.

19. The mixture according to claim 16, wherein the corresponding α-hydroxycarboxylic acid is selected from the group consisting of hydroxyacetic acid, lactic acid, malic acid, α-hydroxyglutaric acid, isocitric acid, tartronic acid, and tartaric acid.

* * * * *

UNITED STATES PATENT AND TRADEMARK OFFICE
CERTIFICATE OF CORRECTION

PATENT NO. : 9,512,061 B2  
APPLICATION NO. : 13/720027  
DATED : December 6, 2016  
INVENTOR(S) : Roland Bou Chedid et al.

Page 1 of 1

It is certified that error appears in the above-identified patent and that said Letters Patent is hereby corrected as shown below:

In the Claims

Column 14, Claim 19, Line 1, "claim 16" should read --claim 15--

Signed and Sealed this
Tenth Day of April, 2018

Andrei Iancu
*Director of the United States Patent and Trademark Office*